United States Patent [19] [11] 4,124,456
Yagupolsky et al. [45] Nov. 7, 1978

[54] METHOD OF TRIS(PERFLUOROALKYL)PHOSPHINE OXIDES

[76] Inventors: Lev M. Yagupolsky, ulitsa Ivana Kudri, 41, kv. 48; Vladimir N. Zavatsky, ulitsa Preobrazhenskaya, 20/6, kv. 39; Valery Y. Semeny, ulitsa A. Navoi, 57, kv. 27, all of Kiev; Konstantin N. Bildinov, ulitsa Admirala Nakhimova, 26, kv. 79, Perm; Petr V. Serebrov, ulitsa Voronezhskaya, 20, kv. 22, Perm; Alevtina A. Goncharenko, ulitsa Voronezhskaya, 20, kv. 25, Perm; Alexandr V. Kirsanov, ulitsa Reiterskaya, 11, kv. 7, Kiev; Mikhail I. Lyapunov, ulitsa Fedoseeva, 13, kv. 15, Perm; Ninel G. Feschenko, ulitsa E. Potie, 11, kv. 67, Kiev, all of U.S.S.R.

[21] Appl. No.: 688,912

[22] Filed: May 21, 1976

[51] Int. Cl.² ............................................. C25B 3/04
[52] U.S. Cl. ................................. 204/59 R; 204/59 F; 260/606.5 P; 260/429 R
[58] Field of Search ............... 260/606.5 P; 204/59 R, 204/59 F

[56] References Cited

U.S. PATENT DOCUMENTS

| 2,519,983 | 8/1950 | Simons | 204/59 F |
| 2,866,824 | 12/1958 | Burg et al. | 260/606.5 P |
| 2,879,302 | 3/1959 | England et al. | 260/606.5 P |
| 3,079,311 | 2/1963 | Hettinger | 204/59 R |
| 3,393,151 | 7/1968 | Dolle et al. | 260/606.5 P X |
| 3,511,761 | 5/1970 | Childs et al. | 204/59 F |
| 3,931,333 | 1/1976 | Neumaier et al. | 260/606.5 P |

OTHER PUBLICATIONS

R. Paul, J. Chem. Soc., p. 574 (1955).
J. Chem. Soc., p. 1565 (1953).
Emeleus, J. Chem. Soc., p. 375 (1959).
Chemical Abstracts, 84, 80520s (1976) Reference Article Published (1975).

Primary Examiner—Helen M. S. Sneed
Attorney, Agent, or Firm—Haseltine, Lake & Waters

[57] ABSTRACT

Novel compounds, viz., tris(perfluoroalkyl)phosphine oxides have the following general formula

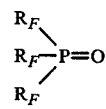

where $R_F$ is a perfluoroalkyl of normal and iso-structure, having from 2 to 8 carbon atoms.

The method of preparing said compounds consists in that trialkylphosphine oxide having the general formula $R_3PO$, where $R = C_8-C_8$, is fluorinated electrochemically in a medium of anhydrous hydrogen fluoride; whenever trialkylphosphine oxides having the general formula $R_3PO$, where $R = C_5 - C_8$, are used as the starting material, they are first brominated in a medium of anhydrous hydrogen fluoride, with subsequent isolation of the end product.

The proposed novel compounds can be used as solvents for salts of rare earth elements and as complexing agents in the separation of valuable metals.

5 Claims, No Drawings

METHOD OF TRIS(PERFLUOROALKYL)PHOSPHINE OXIDES

This invention relates to novel compounds, namely, tris(perfluoroalkyl)phosphine oxides, and to a method of preparing same.

According to the invention, the novel compounds, oxides of tri(perfluoroalkyl)phosphines, are characterized by the general formula

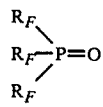

where $R_F$ is a perfluoroalkyl of normal and iso-structure having from 2 to 8 carbon atoms.

Tris(perfluoroalkyl)phosphine oxides can be used as solvents for rare earth elements and as complexing agents in the separation of valuable metals in non-aqueous media, as oleohydrophobic substances when preparing compositions of antipyrenes, and as starting materials for preparing surfactants.

Known in the prior art is a method for preparing tris(trifluoromethyl)phosphine oxide by reacting tris(trifluoromethyl)dichlorophosphoran with oxalic acid (R. Paul J.Chem. Soc., 1955, 574). The starting tris(trifluoromethyl)dichlorophosphoran is prepared by chlorinating, at a low temperature, tris(trifluoromethyl)phosphine (J.Chem.Soc., 1953, 1565) which, in turn, is obtained by reacting critical trifluorodimethane with white and yellow phosphorus at a high temperature (F. Bennet et al., Nature, 166, 225, 1950).

It becomes clear that the process of preparing tris(trifluoromethyl)phosphine oxide is a multi-step procedure (synthesis of trifluorodimethane, tris(trifluoromethyl)phosphine, its chlorination with the resulting tris(trifluoromethyl)dichlorophosphoran, and interaction of the latter with oxalic acid to obtain the end product). The process requires expensive materials; furthermore the materials are lost at each process step, which results in considerable expenditures per unit of the desired product.

Tris(perfluoroalkyl)phosphine oxides having the general formula

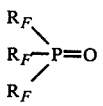

where $R_F$ is a perfluoroalkyl of normal or iso-structure having from 2 to 8 carbon atoms have not been described in the literature.

The novel compounds, tris(perfluoroalkyl)phosphine oxides, are colorless transparent liquids that can be distilled under atmospheric pressure or in vacuum. The physico-chemical constants of said compounds are given in the Table.

The method for preparing said novel compounds is effected as follows.

Oxides of trialkylphosphine having the general formula $R_3PO$, where $R = C_2-C_8$, are fluorinated electrochemically in a medium of anhydrous hydrogen fluoride according to the following scheme:

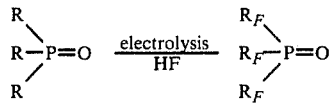

where
R is $C_2H_5$, $n$—$C_3H_7$, $n$—$C_4H_9$, $n$—$C_5H_{11}$, iso—$C_5H_{11}$, $n$—$C_6H_{13}$, $n$—$C_7H_{15}$, $n$—$C_8H_{17}$, and
$R_F$ is $C_2F_5$, $n$—$C_3F_7$, $n$—$C_4F_9$, $n$—$C_5F_{11}$, iso—$C_5F_{11}$, $n$—$C_6F_{13}$, $n$—$C_7F_{15}$, $n$—$C_8F_{17}$.

In order to obtain higher oxides of tris(perfluoroalkyl)phosphines ($C_5$ and over) their hydrocarbon analogues are first brominated in a medium of hydrogen fluoride with from 2 to 6 bromine atoms per molecule of trialkylphosphine oxide. Otherwise trialkylphosphine oxides will be destroyed with breakage of the C—P bond:

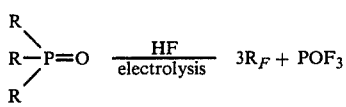

where
R is $C_5H_{11}$, $C_6H_{13}$, $C_7H_{15}$, $C_8H_{17}$, and
$R_F$—$C_5F_{12}$, $C_6F_{14}$, $C_7F_{16}$, $C_8F_{18}$ The bromination of trialkylphosphine oxides is carried out in a polyethylene or a fluoroplastic reactor provided with a reflux condenser and a magnetic stirrer. A mixture consisting of 15-25 percent of hydrogen fluoride and 85-75 percent of trialkylphosphine oxide is prepared in the reactor, and then the required quantity of bromine is added, and the reaction mixture is stirred for 3-4 hours at room temperature.

The obtained reaction mixture is charged into an electrolysis bath containing anhydrous hydrogen fluoride, to make a 10-25 percent phosphine oxide solution in hydrogen fluoride.

The electrochemical fluorination of the brominated trialkylphosphine oxides is done in standard equipment used for preparing perfluorinated organic compounds. As the level of the electrolyte in the bath diminishes, hydrogen fluoride and the starting brominated phosphine oxide are added periodically. The perfluorinated products are collected at the bottom of the electrolyzer and then withdrawn periodically from it. The electrolysis process can be conducted either periodically, or continuously.

The preferable conditions for the electrolysis are current density from 0.02 to 0.05 A/sq.cm, and voltage across the electrodes of 5.0-6.0 V.

The yield of the end products, oxides of tris(perfluoroalkyl)phosphines, is from 10 to 50 percent of theory. The end products are isolated from the mixture of perfluorinated compounds, resulting from the electolysis by the known methods, for example, by processing with calcined sodium fluoride, and rectification.

For a better understanding of the invention, the following examples of its practical embodiment are given by way of illustration.

EXAMPLE 1

A packet type electrolyzer, 1.2 liter capacity, provided with nickel anodes and steel cathodes, is charged with a solution of tripropylphosphine oxide in anhydrous hydrogen fluoride having an initial concentration of 15 percent by weight, that is further maintained within the range of 15-20 percent by weight, by adding regularly the starting solution (80 percent by weight solution of tripropylphosphine oxide in hydrogen fluoride).

The conditions of the process are as follows: current density 0.03 A/sq.cm, voltage across the electrodes 5.5-5.8 V, electrolyte temperature 18°-20° C., temperature in the reflux condenser - 25°-30° C.; current - full-wave rectified.

The electrolysis process is periodic. As the electrolyte level drops, fresh portions of hydrogen fluoride are added. Liquid perfluorinated products (crude product) are collected at the bottom, from where they are withdrawn periodically.

The obtained crude product weighs 356 g, which is 52.2 weight percent of theory.

The average analysis of the crude product by the gas-liquid chromatographic method shows the presence in it of 96.0 percent of perfluoropropylphosphine oxide. The yield of perfluoropropylphosphine oxide is 50.1 percent. The boiling point, 150°-151° C., $n_D^{20}$ 1.2948, $d_n^{20}$ 1.8598.

Found, in percent by weight: P, 5.86, 5.66; C, 19.25, 19.32; F, 70.78, 70.70,71.36. $MR_D$ 55.04. $C_8F_{21}PO$ Calculated, in percent by weight: P, 5.59; C, 19.48; F,72.1. $MR_D$ 55.2.

The I-R spectra of perfluoropropylphosphine oxide are characterized by intense absorption in the region of 1332 cm$^{-1}$ which is characteristic of the P=O bond, and also at 1140 cm$^{-1}$ and 1220cm$^{-1}$, corresponding to the C-F bonds.

EXAMPLE 2

The electrochemical fluorination of triethylphosphine oxide is effected in the same electrolyzer as in Example 1. A solution of 110 g of triethylphosphine oxide in 1.2 liters of hydrogen fluoride is loaded into the apparatus and the process is carried out under conditions similar to those described in Example 1. The electrolysis continued for 15 hours. The current density 0.03 A/sq.cm, voltage across the electrodes 5.2-5.4 V. The yield of perfluorinated products is 43 g. As they are distilled with a reflux condenser, 36 g of tris(perfluoroethyl)phosphine oxide are obtained. This is a colorless transparent liquid boiling at 96°-98° C. $N_D^{20}$ 1.2859, $d_4^{20}$ 1.774.

Calculated: $MR_D$ 40.49, found: $MR_D$ 40.76.

Found in percent by weight: F, 69.96, 71.08; P, 7.75, 7.45.

Formula: $C_6F_{15}OP$. Calculated, in percent by weight: F, 70.6; P, 7.67.

EXAMPLE 3

The electrochemical fluorination is carried out in a steel electrolyzer of 2.4 liter capacity using nickel anodes and cathodes.

2.0 liters of anhydrous hydrogen fluoride and 330 g of tributylphosphine oxide are charged into the electrolyzer in hydrogen fluoride. The process conditions are: current density 0.028 A.sq.cm, voltage across the electrodes 5.8 V, the temperature of the electrolyte 18°-20° C., the temperature in the reflux condenser from −15 to 20° C. The current is full-wave rectified. As the level of the electrolyte lowers, the required quantity of hydrogen fluoride is added to the electrolyzer. Liquid perfluorination products (crude product) are collected at the bottom and withdrawn periodically. The yield of the crude product is 425 g.

50 g of calcined sodium fluoride are added to the crude product in the polyethylene reactor, the mixture is stirred for thirty minutes and filtered. The filtrate is fractionated on a glass column with a reflux condenser, 20 cm high.

The yield of tris(perfluorobutyl)phosphine oxide is 344 g. The boiling point, 185°-187° C. at 760 mm Hg (82°-84° C. at 18 mm Hg) $n_D^{20}$ 1.3038, $d^{20}$ 1.8930.

Found, in percent by weight: F, 73.0, 72.56; P, 4.31, 4.38; $MR_D$ 70.34. $C_{12}F_{27}PO$ Calculated, in percent by weight: F, 72.9; P, 4.4 $MR_D$ 69.977.

In the I-R spectrum, tris(perfluorobutyl)phosphine oxide absorbs intensely at 1356 cm$^{-1}$, which corresponds to the P=O bond.

EXAMPLE 4

A 1-liter polyethylene reactor provided with a magnetic stirrer and a reflux condenser is charged with 250 g (0.96 mole) of triisoamylphosphine oxide, 50 g of hydrogen fluoride, and 308 g (3.84 g-atom) of bromine.

The reaction mixture is kept at room temperature for three hours with stirring, then fluorinated electrochemically under the conditions described in Example 3. The process conditions are:

current density 0.0245 A/sq.cm, voltage across the electrodes 5.9 V, electrolyte temperature 18°-20° C., the temperature is in the reflux condenser from −15° to −20° C.

The yield of crude product is 290 g. The mixture is purified as in Example 1, giving 245 g of tris(perfluoroisoamyl)phosphine oxide. The boiling point, 120°-122° C. at 18 mm Hg; $n_D^{20}$ 1.3102, $d_4^{20}$ 1.9052. Found, in percent by weight: F, 73.64, 74.16; 72.26; P, 3.6; $MR_D$ 85.932; $C_{15}F_{33}PO$.

Calculated, in percent by weight: F, 73.4; P 3.63; $MR_D$ 84.71.

IN the I-R spectrum, tris(perfluoroisoamyl)phosphine oxide absorbs in the region of 1364 cm$^{-1}$ which corresponds to the P=O bond.

EXAMPLE 5

A polyethylene reactor provided with a reflux condenser is charged with 145 g of tri-n-octylphosphine oxide, 40 g of hydrogen fluoride, and 180 g of bromine. The bromination of tri-n-octylphosphine oxide is carried out under the conditions and in the apparatus as described in Example 4.

The electrochemical fluorination of brominated tri-n-octylphosphine oxide is carried out in the apparatus similar to that described in Example 3. The process conditions are: current density 0.0245 A/sq.cm, voltage across the electrodes 6.0 V, the temperature of the electrolyte 18°-20° C., the temperature in the reflux condenser from −15° to −20° C. The yield of crude product is 230 g. It is processed as in Example 1 giving 100 g of tri-(perfluorooctyl)phosphine oxide (b.p. 138°-140° C. at 0.3 mm Hg). $n_D^{20}$ 1.3184; $d_4^{20}$ 1.9480.

Found, in percent by weight: P, 2.68; F, 73.8, $MR_D$ 129.10; $C_{24}F_{51}PO$.

Calculated, in percent by weight: P, 2.38; F, 74.3; $MR_D$ 128.942.

EXAMPLE 6

The process is conducted by following the procedure in Example 4. The yield of tris(n-perfluoroamyl)phosphine oxide is 40 percent by weight of theory. The boiling point, 102°–104° C. at 14 mm Hg. $n_D^{20}$ 1.3080; $d_4^{20}$ 1.9050; $MR_D$ 85.900.

Found, in percent by weight: P, 3.98; F, 73.8. $C_{15}F_{33}PO$.

Calculated, in percent by weight: P, 3.63; F, 73.4; $MR_D$ 84.716.

EXAMPLE 7

The procedure is the same as in Example 4.

The yield of tris(n-perfluorohexyl)phosphine oxide is 36 percent by weight of theory. The boiling point is 143°–144° C. at 14 mm Hg. $n_D^{20}$ 1.3126, $d_4^{20}$ 1.9240.

Found, in percent by weight: P, 3.44; F, 72.9; $MR_D$ 101.21. $C_{18}F_{39}PO$.

Calculated, in percent by weight: P, 3.09; F, 73.6; $MR_D$ 99.45.

EXAMPLE 8

The procedure is the same as in Example 4. The yield of tris(n-perfluoroheptyl)phosphine oxide is 26 percent by weight of theory. the boiling point 121°–123° C. at 0.4 mm Hg. $n_D^{20}$ 1.3146, $d_4^{20}$ 1.9450.

Found, in percent by weight: P, 3.03; $MR_D$ 116.0 $C_{21}F_{45}PO$.

Calculated, in percent by weight; P, 2.69; F, 74.0 $MR_D$ 114.2.

Table
TRIS(PERFLUOROALKYL)PHOSPHINE OXIDES

| Nos | Formula | b.p., °C | $d_4^{20}$ | $d_D^{20}$ | mol. wt. | $MR_D$ calculated, % w/w | $MR_D$ found, %w/w |
|---|---|---|---|---|---|---|---|
| 1. | $(C_2F_5)_3PO$ | 96–98/760 mm Hg | 1.774 | 1.2859 | 404.04 | 40.490 | 40.760 |
| 2. | $(n-C_3F_7)_3PO$ | 150–151/760mm Hg | 1.8598 | 1.2948 | 554.08 | 55.20 | 55.04 |
| 3. | $(n-C_4F_9)_3PO$ | 185–187/760mm Hg  82–84/18 mm Hg | 1.8930 | 1.3038 | 704.1 | 69.974 | 70.340 |
| 4 | $(i-C_5F_{11})_3PO$ | 120–122/18mm Hg  107–109/14mm Hg | 1.9052 | 1.3102 | 854.13 | 84.716 | 85.932 |
| 5. | $(n-C_5F_{11})_3PO$ | 102–104/14mm Hg | 1.9050 | 1.3080 | 854.13 | 84.716 | 85.900 |
| 6. | $(n-C_6F_{13})_3PO$ | 142–144/14mm Hg | 1.9240 | 1.3126 | 1004.16 | 99.458 | 101.21 |
| 7. | $(n-C_7F_{15})_3PO$ | 121–123/0.4mm Hg | 1.9450 | 1.3146 | 1154.19 | 114.20 | 116.00 |
| 8. | $(n-C_8F_{17})_3PO$ | 138–140/0.3mm Hg | 1.948 | 1.3184 | 1304.22 | 128.942 | 129.100 |

We claim:

1. A method of preparing a tris(perfluoroalkyl) phosphine oxide having the formula

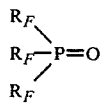

wherein $R_F$ is a perfluoroalkyl of normal or iso-structure having from 2 to 4 carbon atoms comprising electrochemically fluorinating a trialkylphosphine oxide having the formula $R_3PO$, where R is a $C_2$–$C_4$ alkyl and subsequently isolating the fluorinated product.

2. A method of preparing a tris(perfluoroalkyl)phosphine oxide having the formula

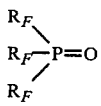

where $R_F$ is a perfluoroalkyl of normal or iso-structure having from 5 to 8 carbon atoms comprising brominating a trialkylphosphine oxide having the formula $R_3PO$, where R is a $C_5$–$C_8$ alkyl, in the presence of hydrogen fluoride, electrochemically fluorinating the bromination reaction mixture and subsequently isolating the fluorinated product.

3. The method of claim 2 in which the electrochemical fluorination is carried out at a current density of 0.02–0.05 A/sq.cm. and voltage across the electrodes of 5–6 V.

4. The method according to claim 1, in which the electrochemical fluorination is carried out at a current density of 0.02–0.05 A/sq.cm and voltage across the electrodes of 5–6 V.

5. The method according to claim 1, in which the bromination of the $C_5$–$C_8$ trialkylphosphine oxide is performed with 2–6 bromine atoms per molecule of trialkylphosphine oxide.

* * * * *